United States Patent [19]

Koch

[11] Patent Number: 5,571,479
[45] Date of Patent: Nov. 5, 1996

[54] CUVETTE

[75] Inventor: Bruno Koch, Cham, Switzerland

[73] Assignee: Hoffmann-La Roche Inc., Nutley, N.J.

[21] Appl. No.: 288,169

[22] Filed: Aug. 10, 1994

[30] Foreign Application Priority Data

Feb. 18, 1994 [CH] Switzerland ............... 489/94

[51] Int. Cl.$^6$ .................................................. B01L 3/00
[52] U.S. Cl. .......................... 422/102; 356/246; 422/104
[58] Field of Search ............................. 356/246; 422/102, 422/104, 58; 220/608, 737; 206/514–520

[56] References Cited

U.S. PATENT DOCUMENTS

| | | | |
|---|---|---|---|
| D. 342,793 | 12/1993 | Balmer | D24/224 |
| 3,627,432 | 12/1971 | Bergmann | 356/246 |
| 3,994,594 | 11/1976 | Sandrock et al. | 356/246 |
| 4,634,576 | 1/1987 | Galle et al. | 356/246 X |
| 5,098,661 | 3/1992 | Froehlich et al. | 422/102 |

FOREIGN PATENT DOCUMENTS

| | | |
|---|---|---|
| 512368 | 4/1992 | European Pat. Off. . |
| 020747 | 9/1991 | WIPO . |

OTHER PUBLICATIONS

Derwent Abstract No. AN–92–374703/46. Apr. 1992.

*Primary Examiner*—Robert J. Warden
*Assistant Examiner*—Krisanne M. Thornton
*Attorney, Agent, or Firm*—George W. Johnston; William H. Epstein; John P. Parise

[57] ABSTRACT

A cell for performing optical measurements in an automatic analyzer is molded in one piece from a transparent plastic material, and has a tubular body including two plane walls parallel to each other, two opposite ends, and a bottom wall. The first end of the tubular body is open and the second end is closed by the bottom wall which has the shape of a half-cylinder. The tubular body of the cell has two side-walls which extend between the plane-parallel walls and which each have an upper portion and a lower portion. The lower portion of each side wall is adjacent the bottom wall and includes an elongated, leg-shaped outer projection which extends along the longitudinal axis of the cell between the upper portion of the side-wall and a point at a certain distance from the bottom wall. Each of the plane-parallel walls has a tongue member adjacent the open end of the tubular body. The tongue members extend outwardly from the border of the open end of the tubular body of the cell in a direction perpendicular to the plane-parallel wall and ends at an outer edge. Each tongue member has an upper surface and a recess, and said tongues and their recesses are positioned symmetrically to each other with respect to the longitudinal axis of the cell. To improve optical properties of the cuvette side walls and bottom wall (used as measuring windows for carrying out electro-optical measurements of the cuvette contents), the outer projection on the side-wall containing is made longer and broader than the outer projection on the opposite side-wall.

9 Claims, 4 Drawing Sheets

CUVETTE

BACKGROUND OF THE INVENTION

1. Field of the Invention

The invention relates to a cell for performing optical measurements in an automatic analyzer, and more particularly, to a single cell for an analyzer for clinical chemical analyses.

2. Description

Cells for performing optical measurements are conventionally filled with samples and reagents in the analyzer. Electro-optical analysis is then carried out on the sample-reagent mixture contained in the cell.

Known analyzers use single reaction cells, also called measuring cells, which are placed on a suitable carrier in the analyzer by a mechanical, automatically-controlled transport device. After use, the reaction cells are removed from the cell carrier. In these analyzers, each cell remains on the cell carrier for the entire period of analysis. Transport of each cell to the cell carrier, and its subsequent removal from the carrier, therefore takes place only once. Thus, the risk of a cell being lost during transport is relatively low.

In modern analyzers which attempt to achieve a high number of measurements per unit of time (in correspondingly short cycle times), it is desirable to carry out certain steps of the analysis process (e.g., addition of reagents to individual cells, carrying out mixing movements of the cells, and so on) outside the cell carrier, and to use the cell carrier predominantly for performing optical measurements on the sample-reagent mixtures in the cells. For this purpose, the transport of each cell to the cell carrier and its removal from the carrier, must be carried out a number of times. The transport system must allow each cell to be transported between the cell carrier and the different processing stations. Some analysis systems operate with rotatable cell carriers. Thus, it may be desirable to transport cells even when the cell carrier is rotating. Consequently, the risk of a cell going astray in such a flexible and repeated transport system is correspondingly higher.

For many applications, loss of a cell in the analyzer system is unacceptable. In otherwise extensively automated analyzers, any possibility of cell loss during transport would necessitate visually monitoring the transport of the cells during analyzer operation. This is a practical impossibility.

A cuvette of the above-mentioned type is described in European Patent Application with publication number EP-A-0 512 368 A2 (see U.S. Ser. No. 08/184,521, filed Jan. 21, 1994). Tests carried out with a cuvette of this type have illustrated the desirability of obtaining improved:

(1) optical properties of the portions of the plane-parallel side-walls and of the bottom of the cuvette used as measuring windows for the optical measurements, and (2) accuracy in positioning the cuvette within the analyzer system.

The subject invention fulfills the need in the art for a cuvette having improved optical properties and accuracy in positioning.

SUMMARY OF THE INVENTION

The invention concerns an optical cell for performing optical measurements in an automatic analyzer and more particularly a single cell for an analyzer for clinical chemical analyses which provides the above-mentioned desirable improvements.

According to the invention the cell is molded in one piece from a transparent plastic material and has a tubular body which has i) two plane walls parallel to each other, ii) two opposite ends, and iii) a bottom wall, the first end is open and the second end is closed by the bottom wall, which has the shape of a half-cylinder. The tubular body of the cell according to the invention has two side-walls which extend between the plane-parallel walls, said side-walls each has an upper portion and a lower portion. The lower portion of each side-wall is adjacent the bottom wall of the cell and includes an elongated, leg-shaped outer projection which extends along the longitudinal axis of the cell between the upper portion of the side-wall and a point at a certain distance from the bottom wall of the cell. The leg shaped outer projection on the side-wall which contains the feeding point (for injection molding) of the cuvette is longer and broader than the leg shaped outer projection on the opposite side-wall. In the cell according to the invention each of the plane-parallel walls has a tongue member adjacent the open end of the tubular body, said tongue member extends outwardly from the border of the open end in a direction perpendicular to the plane-parallel wall and ends at an outer edge. Each tongue has an upper surface and a recess, and said tongues and their recesses are positioned symmetrically to each other with respect to the longitudinal axis of the cell.

A main advantage of the inventive cell as compared with the prior art cell described in European Patent Publication No. EP-A-0 512 368 A2 is that the inventive cell improves optical properties of the portions of the plane-parallel side-walls and the bottom of the cuvette which are used as measuring windows for the optical measurements. This improvement is very important, especially when spectrophotometrical absorbance measurements as well as fluorescence polarization measurements of the cuvette contents are carried out.

In a preferred embodiment of the subject cuvette, each tongue member has two recesses, the central points (centers) of which lie on a straight line which is parallel to the outer edge of the tongue. An advantage of this preferred embodiment over the prior art cuvette described in European Patent Publication No. EP-A-0 512 368 A2 is that the cuvette can be positioned in the analyzer system with greater accuracy. This is very important for obtaining reliable measurement results when electro-optical measurements of the cuvette's contents are performed.

In a preferred embodiment of the inventive cell, the diameter of each recess is approximately half the dimension (i.e., length) of the tongue measured in the direction perpendicular to the plane-parallel walls.

In another preferred embodiment of the inventive cell, the depth of each recess is approximately half the dimension (i.e., thickness) of the tongue, measured in the direction parallel to the plane-parallel walls.

In another preferred embodiment of the inventive cell, each tongue has a zone situated between the circumference of its recess and an outer edge of the tongue. The zone has a flat surface which forms an angle of approximately 45° with a plane perpendicular to the longitudinal axis of the cell. This embodiment has the advantage that the special construction of the tongue makes cooperation between the tongue and the mechanical gripper easier.

BRIEF DESCRIPTION OF THE DRAWINGS

A preferred embodiment of the invention is described below with reference to the accompanying drawings wherein.

DETAILED DESCRIPTION OF THE PREFERRED EMBODIMENTS

Figure 1:
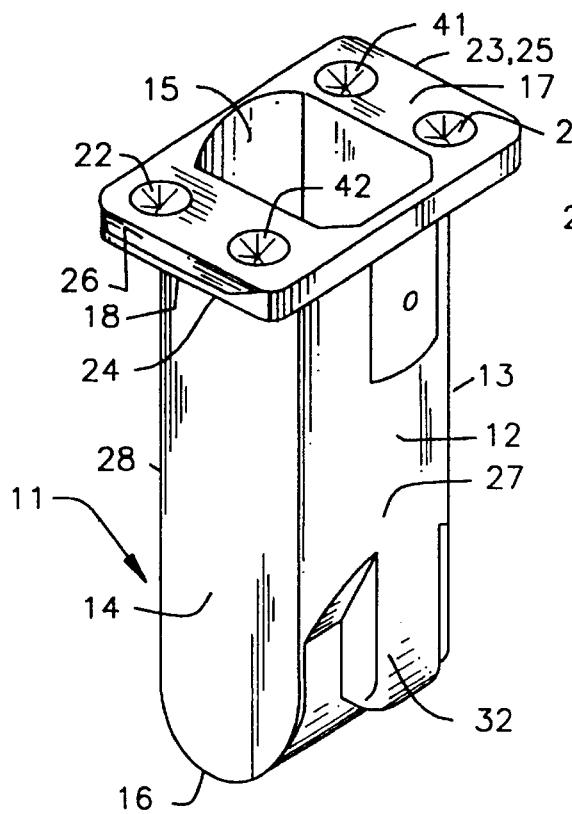
FIG. 1 is a perspective view of a cell according to the invention.
Figure 2:
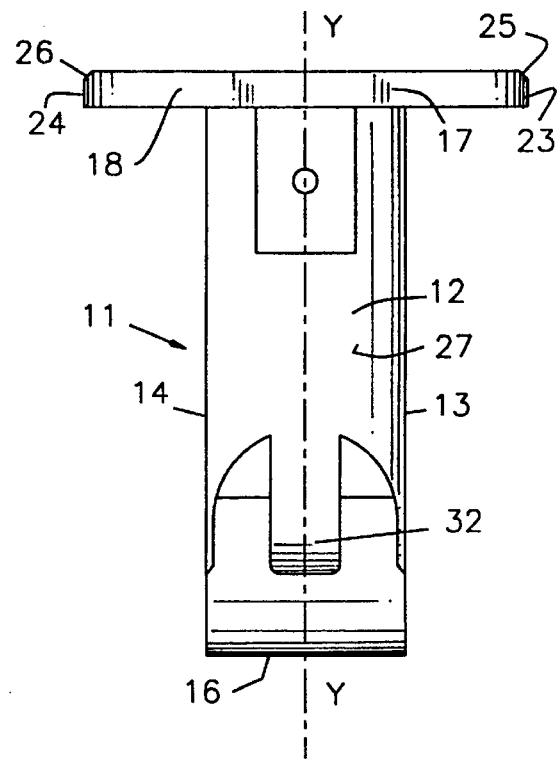
FIG. 2 is a first side elevation of the cell according to FIG. 1.

The subject invention will now be described in terms of its preferred embodiments. These embodiments are set forth to aid in understanding the invention, but are not to be construed as limiting.

The present invention concerns a cell or cuvette for performing optical measurements in an automatic analyzer having a gripping means for transporting the cell. The cell is molded in one piece from a transparent plastic material known in the art. According to the invention, the cell has a tubular body which includes two plane walls positioned parallel to each other and to the longitudinal axis of the cell. The tubular body also has two opposite ends and a bottom wall.

The first end of the tubular body is open to permit entrance of the sample reagent mixture to be measured. The second end is sealed by the bottom wall 16, which has the shape of a half-cylinder. The tubular body has two side-walls which extend between the plane-parallel walls, said side-walls which have each an upper portion and a lower portion. The lower portion of each side wall respectively is adjacent the bottom wall 16 and includes an elongated, leg-shaped outer projection respectively which extends along the longitudinal axis of the cell between the upper portion of the side-wall and a point at a certain distance from the bottom wall, the leg shaped outer projection on the side-wall which contains the feeding point (necessary for manufacture of the cuvette by injection molding) of the cuvette is longer and broader than the leg shaped outer projection on the opposite side-wall.

Each of the plane-parallel walls has a tongue member adjacent the open end of the tubular body. Of course, either a single tongue member or multiple tongue members, having a functionally equivalent configuration, may be used and are to be encompassed by the term "two tongue members." Each tongue member extends outwardly from the open end in a direction perpendicular to the plane-parallel walls and ends at an outer edge. Each tongue member has an upper surface and a recess. The recess is located in the upper surface of the tongue member. The tongue members and their recesses are symmetrically positioned with respect to the longitudinal axis of the cell. The dimensions of the tongue members and their recesses are preselected to permit cooperation with the gripping means of the analyzer by releasably securing the cell to the gripping means.

As shown in the accompanying drawings, cell 11 is a one-piece cuvette which is molded from a transparent plastic, (e.g., a polymethyl-methacrylate injection molding material) by conventional techniques. The construction of this cell makes it suitable for performing optical measurements on the cell contents, which is usually a mixture of a sample and reagents.

The cell 11 has a tubular body 12, which has two plane-parallel walls 13, 14 and two side walls 27, 28. The tubular body 12 is open at one end 15 and closed by a bottom wall 16 at the opposite end. When optical measurements are carried out on the cell contents, a beam of light passes through and perpendicularly to the plane-parallel walls 13, 14 and close to the bottom of the cuvette. The plane-parallel walls are parallel to each other and to the longitudinal axis Y—Y of the cell.

Each of the plane-parallel walls 13, 14 has a tongue 17, 18 located adjacent the open end 15 of the body 12. Each tongue extends from the edge of open end 15 outwardly in a direction perpendicular to the plane-parallel walls 13, 14.

Recesses 21, 41 respectively 22, 42 are located in the upper surfaces of the tongues 17 respectively 18. The tongues and their recesses are symmetrically positioned with respect to the longitudinal axis Y—Y of the cell.

Figure 3:
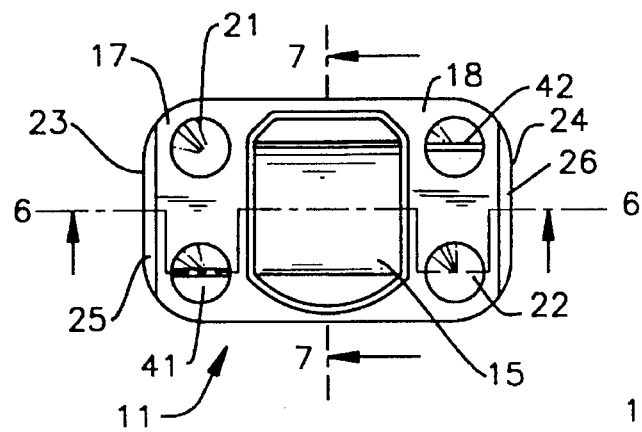
FIG. 3 is a top plan view of the cell according to FIG. 1.
Figure 5:
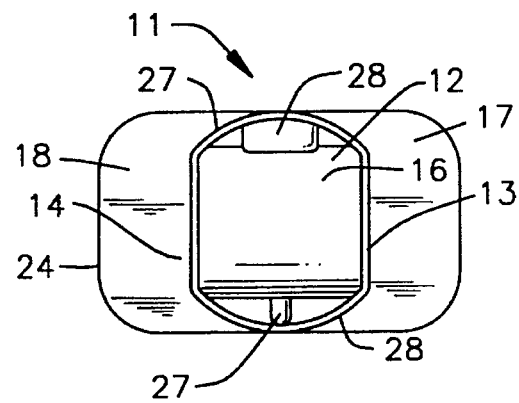
FIG. 5 is a bottom plan view of the cell according to FIG. 1.

As shown by FIG. 3, the central points of recesses 21, 41 respectively 22, 42 lie on a straight line, which is parallel to the outer edges 23, 24 of the tongues 17, 18.

Figure 6:
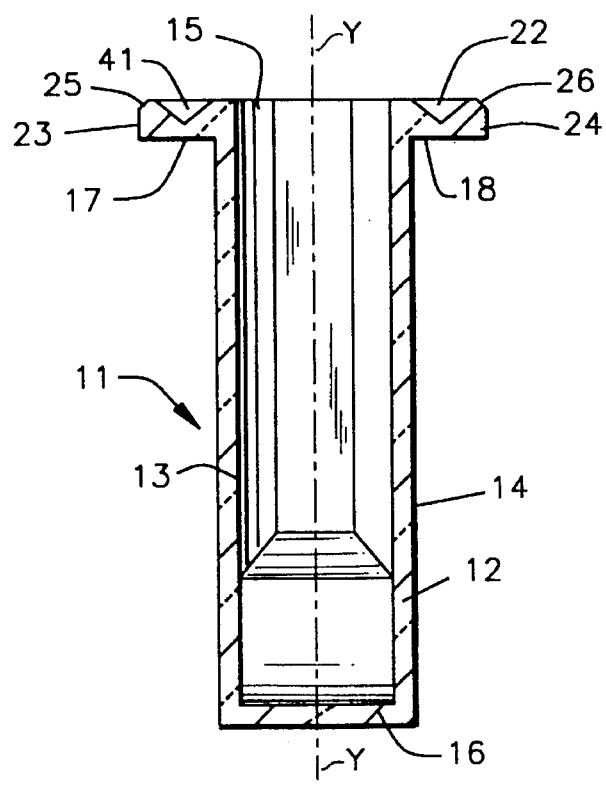
FIG. 6 is a cross-sectional view taken on the line A—A of FIG. 3.

As shown by FIG. 6, each of the recesses 21, 41 respectively 22, 42 has a conical cross-section. Recesses 21, 22 generally have the same shape and dimensions. Recesses 41, 42 also typically have the same shape and dimensions. Recesses 21, 41 respectively 22, 42 are apt to cooperate with gripping means of the analyzer making possible reliable transport and accurate positioning of the cuvette in the analyzer.

As shown by FIG. 3, the upper edge of recesses 21 respectively 22 is circular, whereas the upper edge of each of recesses 41 respectively 42 consists of two half-circles connected by short straight line segments. The advantage provided by this particular shape of recesses 41, 42 is that the otherwise high requirements on the accuracy of the dimensions of the gripper used to transport the cell 11 can be lowered.

The diameter of each of the recesses 21, 22, 41, 42 is preferably approximately half the dimension of the tongue 17, 18 taken in the direction perpendicular to the plane-parallel walls 13, 14. This latter dimension is the length of the tongue taken between the open edge of open end 15 of tubular body 12 of cell 11 and outer edge 23 or 24 of the tongue.

The depth of each of the recesses 21, 22, 41, 42 is preferably approximately half the dimension of the tongue 17 or 18 taken in the direction parallel to the plane-parallel walls 13, 14. This dimension is the thickness of the tongue.

Each tongue 17 and 18 has a zone located between the upper edge (i.e., circumference) of its recesses 21, 41 or 22, 42 and the outer edge 23 or 24 of the tongue. Each of these zones preferably has a flat surface 25 or 26, which forms an angle of approximately 45° with a plane perpendicular to the longitudinal axis Y—Y of the cell.

The above-described construction of the cell 11 makes it optimally suitable for engagement by a gripper (not shown in the drawings) for example, in the form of tongs and forming a portion of a transport device. The gripper is adapted, by means of a conventional drive and appropriate control mechanism for the same, to releasably engage the cell 11 in a predetermined withdrawal position, carry it to a predetermined delivery position, and deliver it there.

When the inventive cell is used for performing spectrophotometrical absorbance measurements of a sample-reagent mixture contained therein, a light beam is transmitted through the lower portion of plan-parallel walls 13, 14, which lower portion is adjacent to bottom wall 16. The lower portions of plan-parallel walls 13, 14, which are used as optical windows for the photometrical measurements, have to satisfy the prescribed optical requirements for performing such measurements.

Since the inventive cell can also be used for performing fluorescence polarization measurements and since for these measurements light leaving the cell through bottom wall 16 needs to be measured, this bottom wall has to satisfy the optical requirements for performing such measurements.

To obtain the desired accuracy when performing fluorescence polarization measurements, the change of light polarization introduced by the optical windows involved (i.e. the respective portions of the plane-parallel walls 13, 14 and the bottom wall 16 of the cell) has to be very low. To obtain this property, during the injection molding process to make the cell, the feeding point has traditionally been located near to the top edge of the cell (i.e. as far as possible from the lower portion of the cell where the optical windows are located). Unfortunately, this choice of location causes, during injection molding of the cell, a confluence of material which gives rise to turbid spots in the plane-parallel walls 13, 14 and in the bottom wall 16, and which is therefore adverse to obtaining the desirable optical properties of the optical windows in the plane-parallel walls 13, 14 and in the bottom wall 16. The above-mentioned choice of the location of the feeding point also creates difficulties for exhausting air present during the injection molding process.

These difficulties are overcome by the unique structure of the inventive cell. As shown by FIGS. 1, 2, 4, 5 and 7, the tubular body 12 has two side-walls 27, 28 which extend between the plane-parallel walls 13, 14. The side-walls 27, 28 each have an upper portion and a lower portion. The lower portion is adjacent the bottom wall 16. The lower portion of each side-wall 27 or 28 includes an elongated, leg-shaped outer projection 31, 32 (or rib member) which extends longitudinally between the upper portion of the side-wall and a point located at some distance from the lowest point of bottom wall 16.

The inclusion of the leg-shaped projections 31, 32 in the structure of the cell makes it possible to avoid the above-mentioned disadvantageous effect of material confluence during the injection molding process used for manufacturing the cell, thereby satisfying the optical requirements of the optical windows in both the plane-parallel walls 13, 14 and the bottom wall 16. The satisfaction of these optical requirements makes the cell suitable for performing spectrophotometrical absorbance measurements as well as fluorescence polarization measurements.

According to the invention a considerable improvement of the optical properties of the bottom wall 16 is obtained by making the leg-shaped outer projection 32, which is located on side-wall 27 on which the feeding point for injection molding of the cuvette is located, longer and broader than the leg-shaped outer projection 31 on the opposite side-wall 28.

In a preferred embodiment of cell 11 which has the dimensions indicated in FIGS. 8–11, projection 31 has a width of 0.8 mm and the axial distance of the lower end of projection 31 from the lowest point of bottom wall 16 is 3.5 mm, and projection 32 has a width of 2.5 mm and the axial distance of the lower end of projection 32 from the lowest point of bottom wall 16 is 1.8 mm.

To permit air exhaust during the injection molding process, projections 31, 32 have a groove positioned along the longitudinal length of the leg and of a preselected narrow dimension (not shown in the enclosed drawings).

Figure 4:
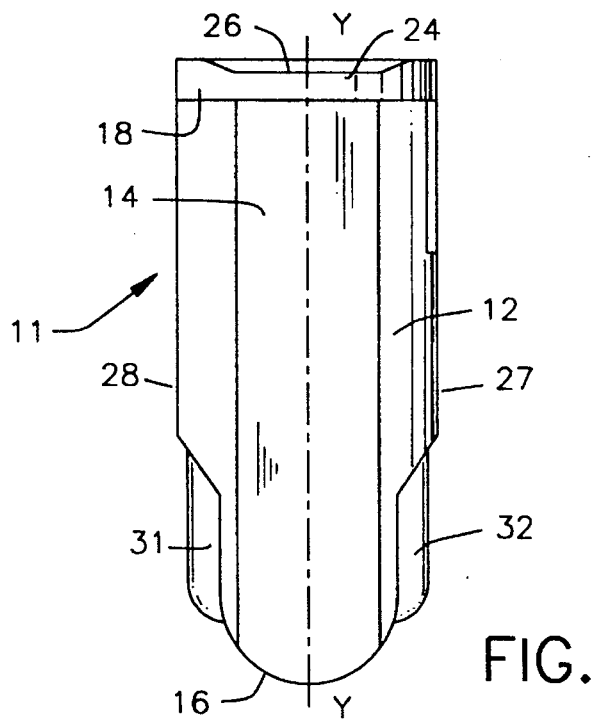
FIG. 4 is a second side elevation of the cell according to FIG. 1.
Figure 7:
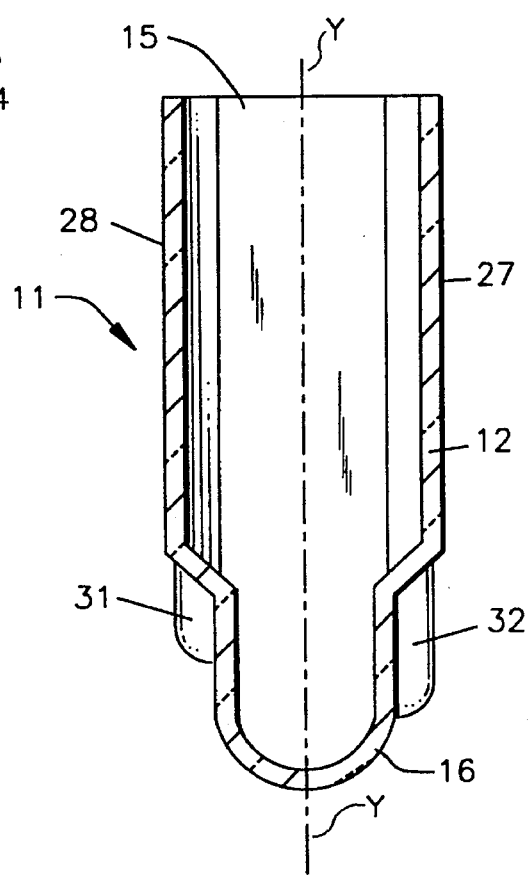
FIG. 7 is a cross-sectional view taken on the line B—B of FIG. 3.
Figure 8:
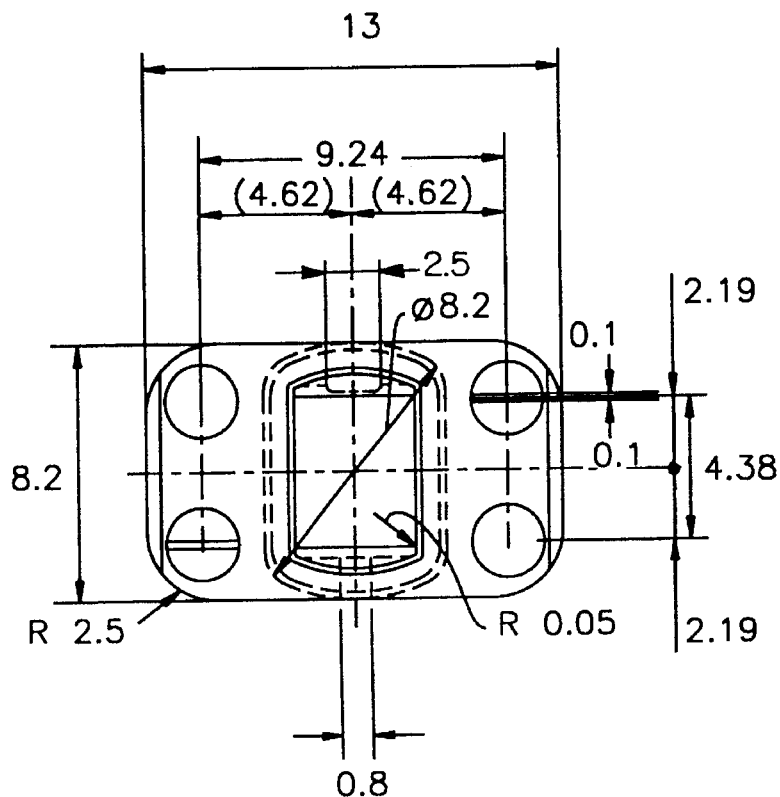
FIGS. 8 to 11 show views including dimensions of the cell according to FIGS. 1–7.
Figure 9:
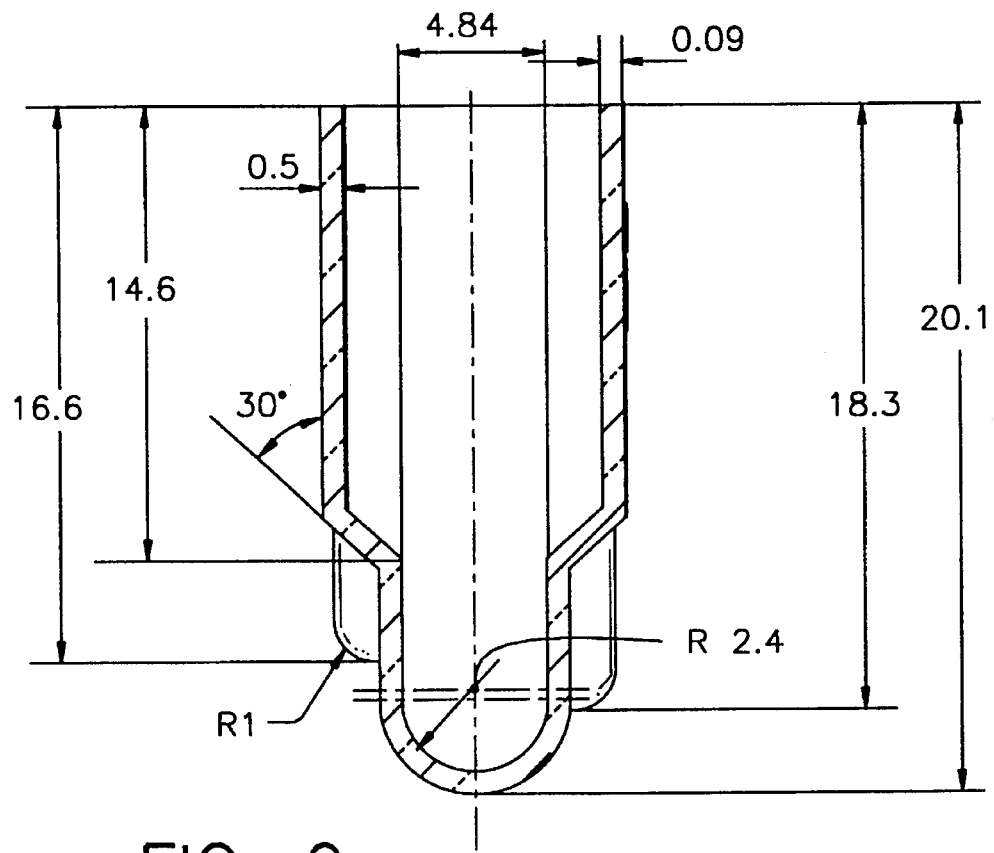
Figures 10, 11:
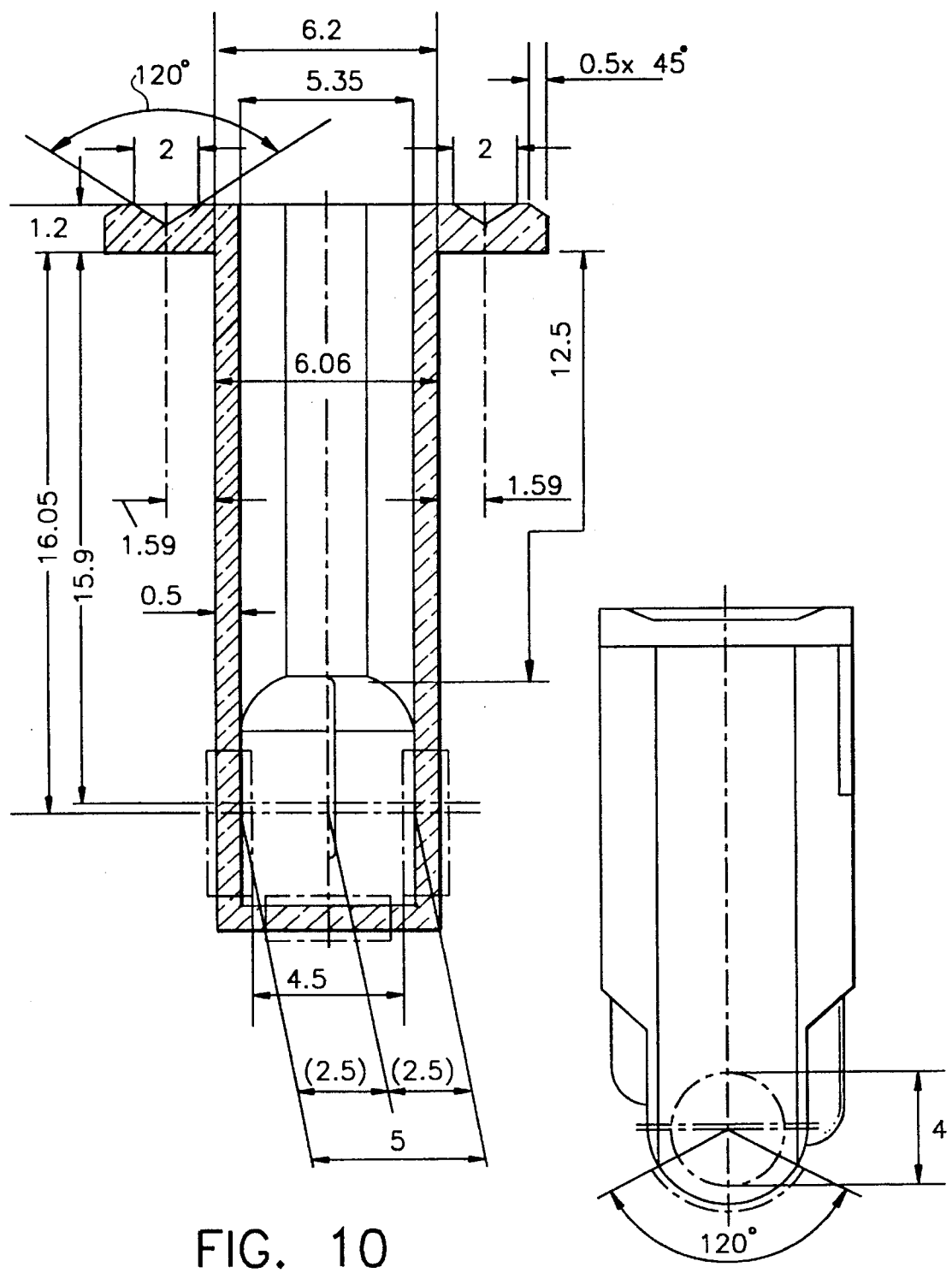

As shown by FIGS. 1, 4 and 7, the bottom wall 16 of the cell preferably is shaped as a half-cylinder which projects outwardly away from tubular body 12.

When used in a clinical chemistry analyzer, cell 11 contains a a sample-reagent mixture and this mixture contains particles in suspension. Within the scope of the invention a light beam having a circular cross-section may be used for performing the electro-optical measurements of the cell contents, i.e. for irradiating a sample-reagent mixture contained therein through the plane-parallel walls 13, 14 of the cell 11. This particular form of the light beam in combination with the preferred half-cylindrical shape of the bottom wall 16 makes it possible to maximize the number of particles irradiated with the light beam. This fact is important in particular for fluorescence polarization measurements, because only a very small fraction of the particles irradiated by the light beam contributes to the intensity of the fluorescent light detected through the bottom wall 16 of the cell 11. The preferred embodiment of the cell 11 having a bottom wall 16 which has the shape of a half-cylinder is therefore particularly advantageous for performing fluorescence polarization measurement, in particular when the amount of the sample-reagent-mixture contained in the cell is very small.

FIGS. 8–11 indicate specific dimensions in millimeters of the cell described above with reference to FIGS. 1–7.

While the invention has been described in conjunction with certain embodiments, it is understood that various modifications and changes may be made without departing from the spirit and scope of the invention. For example, the position and/or relative dimensions of the tongues and recesses may be modified, provided they continue to cooperate with the gripper and can be releasably engaged by the gripper. Moreover, the geometric configuration of the tongue and its recess may be modified subject to the above requirements. The invention is only to be limited by the claims which follow and their equivalents.

What is claimed is:

1. A cell injection molded in one piece from a transparent plastic material for performing optical measurements in an automatic analyzer, which comprises:
    (a) a tubular body having a longitudinal axis and two opposite ends, the first end being open and the second end being closed, and comprising:
        (i) two plane-parallel walls, each plane-parallel wall being parallel to the other plane-parallel wall;
        (ii) a bottom wall which abuts the two plane-parallel walls, configured and dimensioned to close the second end of the tubular body, the bottom wall also having the shape of a half-cylinder; and
        (iii) two side walls which extend between the plane-parallel walls, one of the side walls having a feeding point for injection molding the cell, the side walls each having an upper portion and a lower portion, each lower portion being adjacent the bottom wall, the lower portion of each side wall including an elongated outer projection which extends parallel to the longitudinal axis of the cell between the upper portion of the side wall and a point at a predetermined distance from the bottom wall, the outer projection on the side wall which has the feeding point being longer and broader than the outer projection on the opposite side wall, the configuration and dimensions of both outer projections and the feeding point resulting in a minimized confluence of the transparent plastic material in the bottom wall of the cell; and (b) two tongue members adjacent the open end of the tubular body and extending from each of the plane-parallel walls, each tongue member extending outwardly from the open end of the tubular body in a direction substantially perpendicular to the plane-parallel wall, each tongue member having an upper surface with a recess, each tongue member and its recess being positioned symmetrically relative to the other tongue member and its recess with respect to the longitudinal axis of the cell.

2. The cell of claim 1, wherein each tongue member has at least two recesses and an outer edge, the centers of the recesses lying on a straight line which is parallel to the outer edge of the tongue member.

3. The cell of claim 1, wherein each of the recesses approximates the shape of a cone.

4. The cell of claim 1, wherein the diameter of the upper edge of each recess is approximately half the length of the corresponding tongue member measured in the direction perpendicular to the plane-parallel walls.

5. The cell of claim 1, the depth of each recess is approximately half the thickness of the tongue member measured in the direction parallel to the plane-parallel walls.

6. The cell of claim 1, wherein each tongue has a zone situated between its recess and the outer edge of the tongue, the zone having a flat upper surface which forms an angle of approximately 45° with a plane perpendicular to the longitudinal axis of the cell.

7. The cell of claim 2, wherein each tongue member has two recesses.

8. The cell of claim 7, wherein the upper edge of one of the two recesses has a circular shape, whereas the upper edge of the other recess is formed by two half-circles connected by straight line segments.

9. A cell injection molded in one piece from a transparent plastic material for performing optical measurements in an automatic analyzer, which comprises:

(a) a tubular body having a longitudinal axis and two opposite ends, the first end being open and the second end being closed, and comprising:
  (i) two plane-parallel walls, each plane-parallel wall being parallel to the other plane-parallel wall:
  (ii) a bottom wall which abuts the two plane-parallel walls, configured and dimensioned to close the second end of the tabular body, the bottom wall also having the shape of a half-cylinder; and
  (iii) two side walls which extend between the plane-parallel walls, one of the side walls having a feeding point for injection molding the cell the side walls each having an upper portion and a lower portion, each lower portion being adjacent the bottom wall, the lower portion of each side wall including an elongated outer projection which extends parallel to the longitudinal axis of the cell between the upper portion of the side wall and a point at a predetermined distance from the bottom wall, the outer projection on the side wall which has the feeding point being longer and broader than the outer projection on the opposite side wall, the configuration and dimensions of both outer projections and the feeding point resulting in a minimized confluence of the transparent plastic material in the bottom wall of the cell; and (b) two tongue members adjacent the open end of the tubular body and extending from each of the plane-parallel walls, each tongue member extending outwardly from the open end of the tubular body in a direction substantially perpendicular to the plane-parallel wall, each tongue member having an upper surface with two cone-shaped recesses and an outer edge, the centers of the recesses on each tongue member lying on a straight line which is parallel to the outer edge of the tongue member, each tongue member and its two recesses being positioned symmetrically relative to the other tongue member and its two recesses with respect to the longitudinal axis of the cell.

* * * * *